(12) United States Patent
Nappi (10) Patent No.: US 10,765,778 B2
(45) Date of Patent: Sep. 8, 2020

(54) BIO-RESORBABLE RETICULAR PROSTHESIS AND RELATED MANUFACTURING METHOD

(71) Applicant: Francesco Nappi, Paris (FR)

(72) Inventor: Francesco Nappi, Paris (FR)

(*) Notice: Subject to any disclaimer, the term of this patent is extended or adjusted under 35 U.S.C. 154(b) by 126 days.

(21) Appl. No.: 15/523,840

(22) PCT Filed: Nov. 2, 2015

(86) PCT No.: PCT/IB2015/058458
§ 371 (c)(1),
(2) Date: May 2, 2017

(87) PCT Pub. No.: WO2016/071823
PCT Pub. Date: May 12, 2016

(65) Prior Publication Data
US 2017/0326274 A1    Nov. 16, 2017

(30) Foreign Application Priority Data

Nov. 3, 2014   (IT) .............................. RM2014A0635

(51) Int. Cl.
*A61F 2/90*    (2013.01)
*A61L 27/48*    (2006.01)
(Continued)

(52) U.S. Cl.
CPC ................ *A61L 27/48* (2013.01); *A61F 2/90* (2013.01); *A61L 27/50* (2013.01); *A61L 27/507* (2013.01);
(Continued)

(58) Field of Classification Search
CPC ................................................. A61F 2/82–915
See application file for complete search history.

(56) References Cited

U.S. PATENT DOCUMENTS

| | | | | |
|---|---|---|---|---|
| 4,743,480 A | * | 5/1988 | Campbell | ............... B29C 48/30 |
| | | | | 428/36.5 |
| 2004/0098095 A1 | * | 5/2004 | Burnside | ................... A61F 2/07 |
| | | | | 623/1.13 |

(Continued)

FOREIGN PATENT DOCUMENTS

| EP | 0633032 B1 | 2/2001 |
|---|---|---|
| WO | 2005072649 A1 | 8/2005 |
| WO | 2007092583 A2 | 8/2007 |

OTHER PUBLICATIONS

International Search Report dated Jan. 27, 2016 from International Application No. PCT/IB2015/058458, 3 pages.
(Continued)

*Primary Examiner* — Suba Ganesan
(74) *Attorney, Agent, or Firm* — Meunier Carlin & Curfman LLC (57) ABSTRACT

The present invention concerns a bio-resorbable prosthesis (1, 1') for organs with lumens, as blood vessels and the like, comprising at least one bio-absorbable material layer (2), intended to be arranged in contact with said lumen organ when said prosthesis (1, 1') is implanted, and at least one auxetic material layer (3), arranged in contact with said at least one bio-absorbable material layer (2).
The present invention also concerns a method for the production of a bio-absorbable prosthesis (1, 1').

13 Claims, 9 Drawing Sheets

(51) Int. Cl.
- A61L 27/50 (2006.01)
- A61L 31/12 (2006.01)
- A61L 31/14 (2006.01)
- C08L 27/18 (2006.01)

(52) U.S. Cl.
CPC .............. *A61L 31/129* (2013.01); *A61L 31/14* (2013.01); *C08L 27/18* (2013.01); *A61F 2210/0004* (2013.01); *A61F 2210/0076* (2013.01); *A61F 2250/0031* (2013.01)

(56) References Cited

U.S. PATENT DOCUMENTS

| | | | |
|---|---|---|---|
| 2006/0129227 A1* | 6/2006 | Hengelmolen | A61F 2/91 623/1.16 |
| 2006/0184237 A1* | 8/2006 | Weber | A61F 2/07 623/1.44 |

OTHER PUBLICATIONS

Written Opinion of the International Searching Authority dated Jan. 27, 2016 from International Application No. PCT/IB2015/058458, 5 pages.

Bonhoeffer, Philipp et al. "Transcatheter Implantation of a Bovine Valve in Pulmonary Position: A Lamb Study", Circulation. 2000; 102:813-816.

Carrel, Thierry et al. "Preliminary results following reinforcement of the pulmonary autograft to prevent dilatation after the Ross procedure", The Journal of Thoracic and Cardiovascular Surgery, vol. 136, No. 2, Aug. 2008, pp. 472-475.

Hörer, Jürgen et al. "Neoaortic Root Diameters and Aortic Regurgitation in Children After the Ross Operation", The Society of Thoracic Surgeons, 2009;88:594-600.

Holzapfel, Gerhard A. et al. "Modelling the layer-specific three-dimensional residual stresses in arteries, with an application to the human aorta", J.R. Soc. Interface (2010) 7, 787-799.

Sievers, Hans-Hinrich et al. "A multicentre evaluation of the autograft procedure for young patients undergoing aortic valve replacement: update on the German Ross Registry", European Journal of Cardio-Thoracic Surgery, 49 (2016) 212-218.

Nappi F, Fraldi M, Spadaccio C, et al. Biomechanics drive histological wall remodeling of neoaortic root : A mathematical model to study the expression levels of ki 67, metalloprotease, and apoptosis transition. J Biomed Mater Res A 2016 ;104 :2785-93.

Spadaccio C, Nappi F, De Marco F, Sedati P, Sutherland FW, Chello M, Trombetta M, Rainer A. Preliminary In Vivo Evaluation of a Hybrid Armored Vascular Graft Combining Electrospinning and Additive Manufacturing Techniques. Drug Target Insights. Feb. 28, 2016 ;10(Suppl 1) :1-7. doi : 10.4137/DTI.S35202. eCollection 2016.

Nappi F, Spadaccio C, Fouret P, et al. An experimental model of the Ross operation : Development of resorbable reinforcements for pulmonary autografts. J Thorac Cardiovasc Surg 2015 ;149 :1134-42.

Nappi F, Spadaccio C, Fraldi M, et al. A composite semiresorbable armoured scaffold stabilizes pulmonary autograft after the Ross operation: Mr Ross's dream fulfilled. J Thorac Cardiovasc Surg 2016;151:155-64.e1.

Spadaccio C, Montagnani S, Acar C, et al. Introducing bioresorbable scaffolds into the show. A potential adjunct to resuscitate Ross procedure. Int J Cardiol 2015;190:50-2.

Nappi F, Carotenuto AR, Di Vito D, et al. Stress-shielding, growth and remodeling of pulmonary artery reinforced with copolymer scaffold and transposed into aortic position. Biomech Model Mechanobiol 2016 ;15 :1141-57.

Nappi F, Carotenuto AR, Cutolo A, et al. Compliance mismatch and compressive wall stresses drive anomalous remodelling of pulmonary trunks reinforced with Dacron grafts. J Mech Behav Biomed Mater 2016 ;63 :287-302.

Holmes DR Jr., Firth BG, Wood DL. Paradigm shifts in cardiovascular medicine. J Am Coll Cardiol 2004 ;43 :507-12.

Kereiakes DJ, Ellis SG, Metzger DC, Caputo RP, Rizik DG, Teirstein PS, Litt MR, Kini A, Kabour A, Marx SO, Popma JJ, Tan SH, Ediebah DE, Simonton C, Stone GW ; ABSORB III Investigators Clinical Outcomes Prior to and Following Complete Everolimus-Eluting Bioresorbable Scaffold Resorption : Five-Year Follow-Up From the ABSORB III Trial. Circulation. Sep. 25, 2019. doi : 10.1161/CIRCULATIONAHA.119.042584. [Epub ahead of print].

Stone GW, Kimura T, Gao R, Kereiakes DJ, Ellis SG, Onuma Y, Chevalier B, Simonton C, Dressler O, Crowley A, Ali ZA, Serruys PW. Time-Varying Outcomes With the Absorb Bioresorbable Vascular Scaffold During 5-Year Follow-up : A Systematic Meta-analysis and Individual Patient Data Pooled Study. JAMA Cardiol. Sep. 27, 2019. doi : 10.1001/jamacardio.2019.4101. [Epub ahead of print].

Bangalore S, Kumar S, Fusaro M, Amoroso N, Attubato MJ, Feit F, Bhatt DL, Slater J. Short- and long-term outcomes with drug-eluting and bare-metal coronary stents : a mixed-treatment comparison analysis of 117 762 patient-years of follow-up from randomized trials. Circulation. 2012 ;125 :2873-2891.

Palmerini T, Benedetto U, Biondi-Zoccai G, Della Riva D, Bacchi-Reggiani L, Smits PC, Vlachojannis GJ, Jensen LO, Christiansen EH, Berencsi K, Valgimigli M, Orlandi C, Petrou M, Rapezzi C, Stone GW. Long-Term Safety of Drug-Eluting and Bare-Metal Stents : Evidence From a Comprehensive Network Meta-Analysis. J Am Coll Cardiol. 2015 ;65 :2496-2507.

Nakazawa G, Otsuka F, Nakano M, Vorpahl M, Yazdani SK, Ladich E, Kolodgie FD, Finn AV, Virmani R. The pathology of neoatherosclerosis in human coronary implants bare-metal and drug-eluting stents. J Am Coll Cardiol. 2011 ;57 :1314-1322.

Otsuka F, Vorpahl M, Nakano M, Foerst J, Newell JB, Sakakura K, Kutys R, Ladich E, Finn AV, Kolodgie FD, Virmani R. Pathology of second-generation everolimus-eluting stents versus first-generation sirolimus- and paclitaxel-eluting stents in humans. Circulation. 2014 ;129 :211-223.

Serruys PW, Chevalier B, Sotomi Y, Cequier A, Carrié D, Piek JJ, Van Boven AJ, Dominici M, Dudek D, McClean D, Helqvist S, Haude M, Reith S, de Sousa Almeida M, Campo G, Iniguez A, Sabate M, Windecker S, Onuma Y. Comparison of an everolimus-eluting bioresorbable scaffold with an everolimus-eluting metallic stent for the treatment of coronary artery stenosis (ABSORB II): a 3 year, randomised, controlled, single-blind, multicentre clinical trial. Lancet. 2016 ;388 :2479-2491.

Kereiakes DJ, Ellis SG, Popma JJ, Fitzgerald PJ, Samady H, Jones-McMeans J, Zhang Z, Cheong WF, Su X, Ben-Yehuda O, Stone GW. Evaluation of a fully bioresorbable vascular scaffold in patients with coronary artery disease : Design of and rationale for the ABSORB III randomized trial. Am Heart J. 2015 ;170 :641-651 e3.

Raber L, Brugaletta S, Yamaji K, O'Sullivan CJ, Otsuki S, Koppara T, Taniwaki M, Onuma Y, Freixa X, Eberli FR, Serruys PW, Joner M, Sabate M, Windecker S. Very Late Scaffold Thrombosis : Intracoronary Imaging and Histopathological and Spectroscopic Findings. J Am Coll Cardiol. 2015 ;66 :1901-1914.

\* cited by examiner

BIO-RESORBABLE RETICULAR PROSTHESIS AND RELATED MANUFACTURING METHOD

FIELD OF THE INVENTION

The present invention relates mainly to a reticular, or cross-linked, prosthesis, which is partially bio-resorbable.

More specifically, the invention relates to a prosthesis of the type mentioned, designed and built specifically to reinforce vascular structures in various types of surgery, such as, for example, the grafting of the of the pulmonary artery trunk or the implantation of stents, these vascular structures being potentially capable of changing their elasto-mechanical properties and to grow over time.

BACKGROUND OF THE INVENTION

As is well known, in modern surgery there are various prostheses for the treatment of many types of vascular diseases. In particular, vascular prostheses—used in cardiac surgery, vascular surgery and in invasive cardiology—can be ideally divided into extravascular prostheses, intended to be implanted on the outer surface of the vessels, and intravascular prostheses, better known as endoprostheses, which, in general, are implantable within vessel or vascular structures.

For example, in the field of cardiac surgery, and in particular in pediatric cardiac surgery, it is well known the so-called Ross Procedure, which uses the autologous pulmonary artery (so-called pulmonary autograft) to replace the aortic root, with a replanting of the coronary arteries. In the following, reference will be made also to the technique of so-called Freestanding Ross Root Replacement, to indicate that surgical procedure wherein the pulmonary valve and the pulmonary artery trunk are used as ideal substitutes for pathological aortic valve replacement in block with the aortic root. (Sievers et al *A multicentre evaluation of the autograft procedure for young patients undergoing aortic valve replacement: update on the German Ross Registry † Eur J Cardiothorac Surg.* 2015 Feb. 9. pii: ezv001).

Currently, the Ross Procedure is considered one of the most appropriate procedures for the treatment of aortic valve pathology in children and young adults, as it brings significant advantages in both surgical results and patient management as well as in long-term results.

The transposition of the pulmonary artery trunk in the aortic position, in fact, avoids the known drawbacks of anticoagulation—which usually occurs in conjunction with the use of mechanical prostheses—and provides excellent results in terms of valve hemodynamics.

However, the major drawback of this procedure is represented, in the long term, by the dilatation of the pulmonary artery autograft in the aortic root position. This phenomenon leads to complications, such as the appearance of an aortic regurgitation due to excessive tension on the commissure, the progressive increase of the diameter of the pulmonary artery autograft and, exceptionally, acute dissection of the pulmonary trunk in the aortic position. These complications often imply the need for a new surgical intervention, which is carried out a few years after the first procedure.

To overcome the above drawbacks, a modified procedure has been developed, which involves the use of an extravascular prosthesis, consisting of a synthetic, non-resorbable reinforcement of the pulmonary artery autograft. This extravascular prosthesis is normally made of a synthetic material such as Dacron, tetrapolyethylene or Polytetrafluoroethylene (PTFE).

However, in this type of surgery the use of synthetic materials involves long-term clinical and biological disadvantages. A first important drawback is represented by the inability of such materials to adjust to the biological tissue during the structural development of the vessel. For example, the tetrapolyethylene has a stiffness approximately 24 times greater than the stiffness of the native aorta. Therefore, the ability of the prosthesis to conform to the vessel to which it is applied is very low. This causes the loss of elastomechanical properties and of the "Windkessel" function of the neoaortic root, with retrograde effect on the aortic valve, leading ultimately to its incompetence.

A further disadvantage of these solutions according to the known art is represented by the strong inflammatory reaction caused by the aforementioned synthetic materials, which would lead to a damage to the vitality of the pulmonary artery autograft, interfering with the normal arterialization process.

Conversely, the treatment of aneurysmatic disease of the aorta, peripheral and cerebral vessels majorly relies in the use of intravascular prostheses or vascular stents, i.e. mesh-like cylindrical structures intended to be introduced in the vascular lumen so that they can expand until their diameter is equal to that of the lumen.

Some of the stents presently available are made of an auxetic material, i.e. a material having a negative Poisson ratio. Expanded Polytetrafluoroethylene (Expanded PTFE), also known by the common trade name Goretex®, is an example of auxetic material. When subjected to a tensile stress, the fibers of such material "open up" structurally and the material expands in the direction transverse to the stress. On the contrary, if this material were subject to compression, it would "close" structurally.

One of the problems of the abovementioned intravascular prosthesis is that often they are not able to adapt their conformation or compliance over time to the patient's tissue, especially to vessels of large lumen which tend to grow.

WO2007/092583 discloses a poly(diol citrates)-based coating for implantable devices.

EP0633032 discloses an anti-bacterial vascular prosthesis.

SUMMARY OF THE INVENTION

The technical problem posed and solved by the present invention is that of providing a prosthesis—in particular an extravascular prosthesis configured for use in the Ross procedure as a support and/or reinforcement for the pulmonary artery autograft or an intravascular stent—which is capable of overcoming the disadvantages mentioned above in conjunction with the known art.

Such a problem is solved by a prosthesis according to claim 1.

Preferred features of the invention are provided in the dependent claims.

It is an object of the present invention to provide an extravascular prosthesis able to ensure the physiological growth of the pulmonary artery transposed in the aortic position and then subjected to systemic pressure, which physiological growth is not possible with the known art solutions. In fact, the pulmonary artery is normally subjected to regimes of maximal venous pressure of 35 mmHg wherein, after the transposition at the aortic root, it is subjected to a pressure of 120 mmHg with a potential consequent tendency to dilation.

It is another an object of the present invention to provide a prosthesis configured to give structural support to the pulmonary artery autograft, which bears systemic pressure and allows the process of structural modification of the vascular wall for the preservation of the viability of the graft.

Another object of the invention is to propose a prosthesis provided with a suitable reinforcement, capable of influencing the elastomechanical properties of the neoaortic root or vessel to which it is applied, conferring resistance to dilatation and behavior of conformability and compliance.

A further object of the present invention is to propose an intravascular prosthesis suitable to be implanted as a stent in vessels subject to aneurysmal degeneration as aorta or cerebral vessel.

It is an additional object of the present invention to propose an intravascular prosthesis (stent) with a geometry capable of providing a support, which prosthesis is alternative to current stents for biophysical mechanical properties, in particular for implantation in vessels of small caliber such as the coronary arteries and cerebral vessels.

As will be explained in greater detail in the following sections, the specific selection of materials as well as the selected reticular structure of the prosthesis as expressed in the annexed claims, achieve important technical effects. In particular, the prosthesis of the invention allows a process of guided remodeling of the vessel the prosthesis is applied to, the attainment of optimal growth results of such vessel as well as an improvement in the elasto-mechanical properties of both the vessel per se and the composite body formed by vessel plus prosthesis.

BRIEF DESCRIPTION OF THE DRAWINGS

The present invention will now be described for illustrative but not limitative purposes, according to its preferred embodiments, with particular reference to the figures of the accompanying drawings, wherein:

FIG. 3b shows a side view of the prosthesis of FIG. 3a;

FIG. 3c shows a cross-section of the prosthesis of FIG. 3a;

FIG. 3d shows a schematic perspective view of a layer of bio-absorbable material of the prosthesis of FIG. 3a;

FIG. 7bis shows a graph related to an evolution of the outer diameters of the vascular structure with or without a reinforcement applied;

FIG. 8b shows a side view of the prosthesis of FIG. 8a;

FIG. 8c shows a cross-section of the prosthesis of FIG. 8a;

FIG. 8d shows a perspective view of the layer of bio-absorbable material of the prosthesis of FIG. 8a;

FIG. 9b shows a side view of the prosthesis of FIG. 9a;

FIG. 9c shows a cross-section of the prosthesis of FIG. 9a;

FIG. 9d shows a perspective view of the layer of bio-absorbable material of the prosthesis of FIG. 9a;

In the above figures, similar or corresponding elements will be denoted by the same reference numeral.

DETAILED DESCRIPTION OF PREFERRED EMBODIMENTS

In the following, the description will be directed to an extravascular prosthesis for supporting the pulmonary artery trunk and to an intravascular stent, but the invention should not be considered limited to these specific uses.

Figure 1:
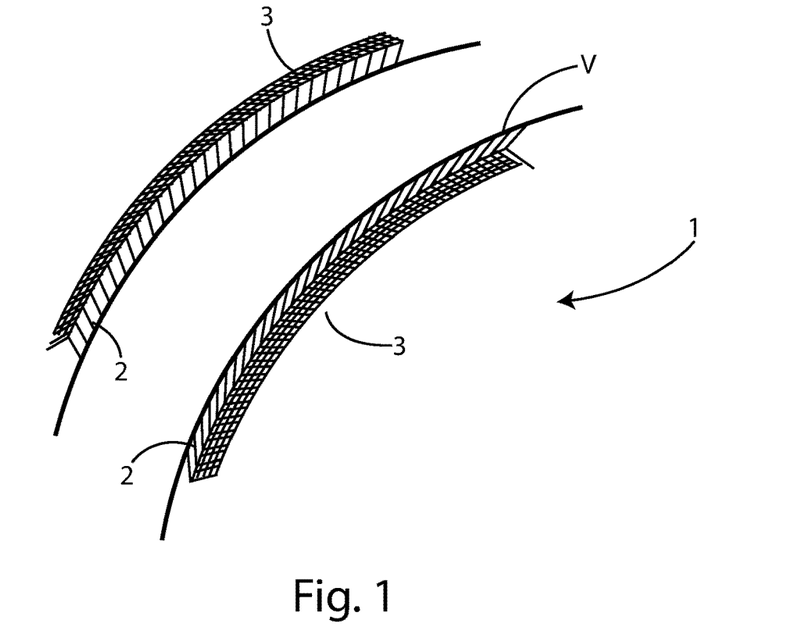
FIG. 1 shows schematically a first embodiment of a reticular prosthesis according to the present invention.
Figure 2:
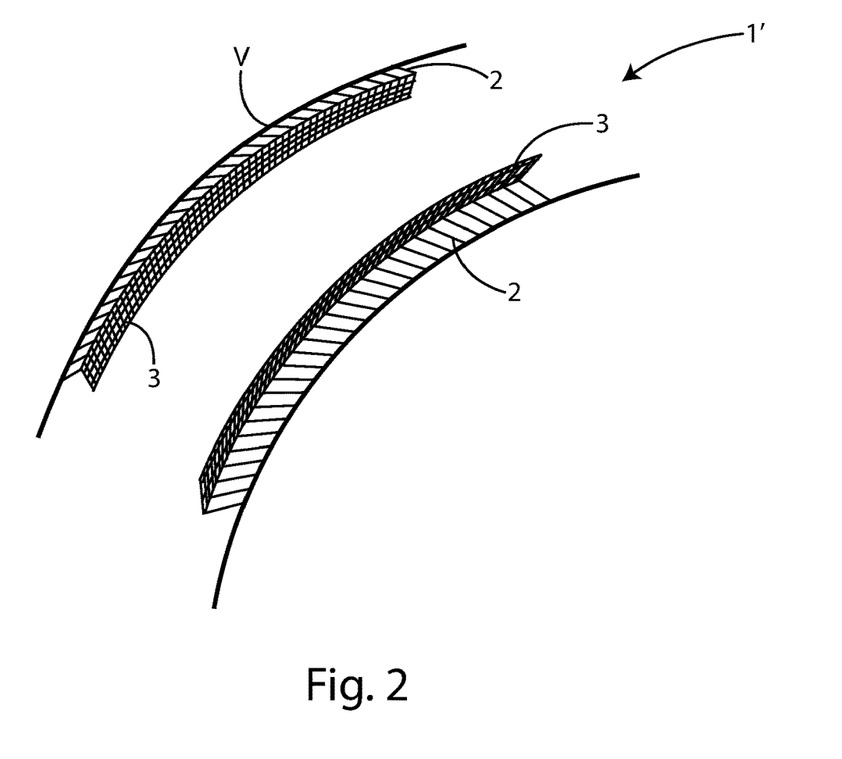
FIG. 2 shows schematically a second embodiment of a reticular prosthesis according to the present invention.

Referring to FIGS. 1 and 2, there are presented two distinct embodiments of a vascular prosthesis according to the invention, denoted by 1 and 1', respectively. Prosthesis 1, 1' has a cross-linked, or mesh-like or reticular, structure and it is partially resorbable, as explained below.

In particular, FIG. 1 schematically shows an extravascular prosthesis 1, while FIG. 2 shows an intravascular prosthesis 1'.

Extravascular prosthesis 1 is configured to be implanted at a pulmonary autograft in a Ross procedure and it is capable of ensuring the physiological growth of the pulmonary artery transposed in the aortic position and then subjected to systemic pressure.

Intravascular prosthesis 1' is configured to be implanted as a stent in vessels undergoing further growth.

The prosthesis 1, 1' essentially comprises at least one layer 2 of bio-absorbable, or resorbable, material, which is intended and configured to be disposed in contact with the organ with lumen when the prosthesis is implanted.

The prosthesis 1, 1' further comprises at least one layer 3 of auxetic material, arranged in contact with said layer of bio-absorbable material 2.

In the case of extravascular prosthesis 1, the layer of bio-absorbable material 2 is disposed to contact the outer side (adventitia) of the vessel; instead, in the case of intravascular prosthesis 1', said layer of bio-absorbable material 2 is contact with the endothelium, which is the innermost part of the tunica intima of the vessel.

The layer 3 of auxetic material is capable of preserving the dilation of the pulmonary autograft subjected to systemic pressure—and in general of supporting the vessel the prosthesis is applied to—ensuring a physiological growth.

The layer 2 realized with bio-resorbable material acts as a scaffold and plays a mechanic role only at the first stages after implantation of the prosthesis, when still not reabsorbed. In fact, the main function of said layer 2 of bioabsorbable material is to stimulate, with its reabsorption, the extracellular matrix and the endogenous reparative reserves present in it to induce those biological changes that lead to a process of complete and homogeneous arterialization of the pulmonary graft—and in general of the vessel the prosthesis is applied to—allowing for an elastic remodeling of the vessel.

In extravascular prosthesis 1, the containment provided by the rigid auxetic material compensates for the stress related to blood pressure, gradually accompanying the process of growth of the vascular structure with its geometric changes, adjusting the reabsorption of the scaffold realized with bio-resorbable material layer 2.

In a most preferred embodiment, the layer 3 of auxetic material is made of expanded polytetrafluoroethylene (so-called Goretex®).

Most advantageously, in the present embodiment the bio-absorbable layer 2 is made of polydioxanone (PDS). Most preferably, layer 2 consists of polydioxanone (PDS) only.

Other embodiments may use different types of bio-absorbable materials, in addition to—or in substitution for—polydioxanone (PDS). Typically, these materials are bioresorbable scaffold (structures) made of monoplymer and/or co-polymer.

Among these materials it may be indicated chemical substances such as polyglycolic acid, acid, poly-l-lactic acid, poliglactin (Vicril®), or the copolymer poly-l-lactic acid-co-ε-caprolactone alone or assembled.

The assembly of such scaffolds may also involve the inclusion of gradual drugs release.

Prosthesis 1, 1'- and each of its layers 2, 3—has a cylindrical shape.

As explained in greater detail below, preferably each of the layers 2 and 3 has a reticular, meaning lattice, mesh-like or cross-linked, construction, being made substantially of thread-shaped structural elements.

The vascular prosthesis 1, 1' has, as mentioned, improved mechanical properties variable and adaptable over time.

Referring now to FIGS. 3a-3d, in extravascular prosthesis 1 the bio-resorbable material layer 2 has the shape of a lattice. Said lattice configuration, in the present example, presents cells 200 of hexagonal shape. Other embodiments may provide for a different polygonal shape of the cells, e.g. triangular, square or rectangular. Preferably, a maximal transverse or longitudinal dimension $Tr_{max}$ of a cell 200 is about 0.2-0.3 mm.

The layer of auxetic material 3 is disposed and coupled externally with respect to said layer of bio-absorbable material 2 and comprises a plurality of longitudinal lateral strips 31, having an auxetic behavior, and a plurality of transverse wires 32, which connect each longitudinal strip 31 with two adjacent strips.

Each longitudinal strip 31 has a bellows-like structure, which makes the strip extensible in the longitudinal direction. The bellows structure of each strip 31 is made, in the present example, by two longitudinal elements, or wires, 311 spaced-part in the transverse direction. The two longitudinal elements 311 have a zigzag development in the undeformed configuration of FIG. 3a and are mutually arranged so that they have, alternatively, a minimal transverse distance $d_{min}$ and a maximal transverse distance $d_{max}$. In the present example, at each occurrence of the minimal distance $d_{min}$ the elements 311 are joined by a transverse element 312.

Figure 3A:
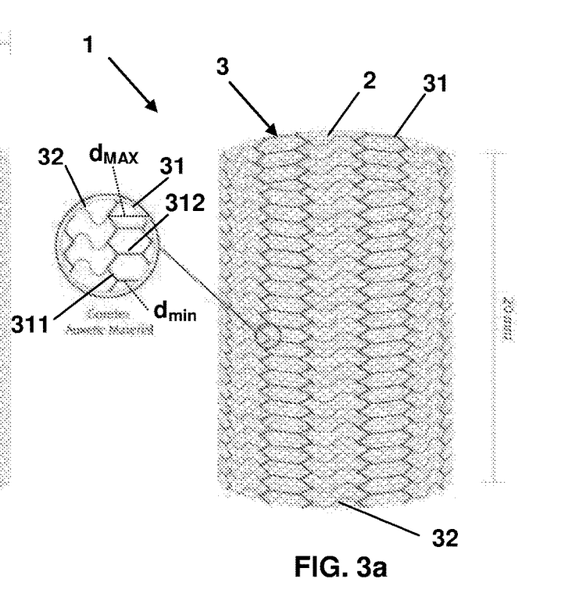
FIG. 3a shows a perspective view of the prosthesis of FIG. 1 in an initial retracted configuration, i.e. immediately after its implantation.
Figure 3B:
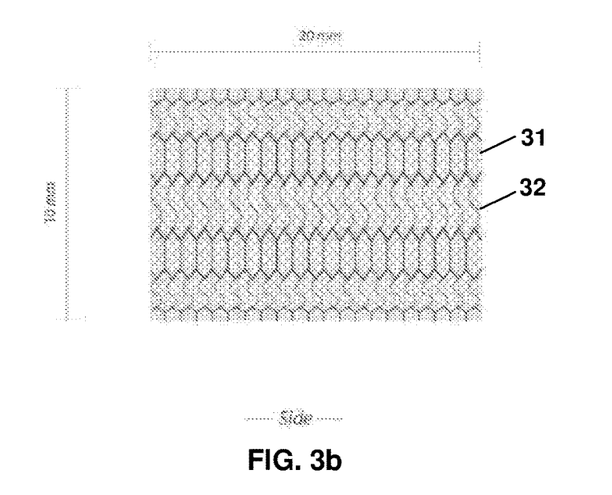
Figure 3C:
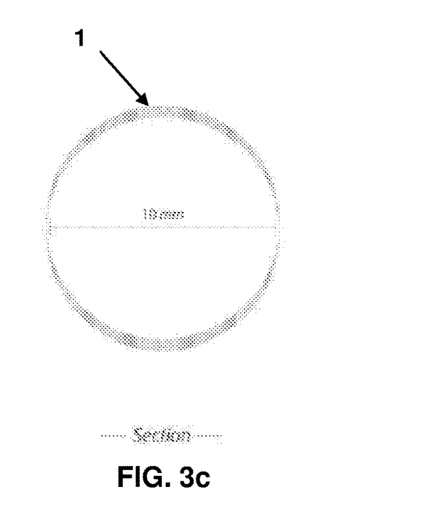
Figure 3D:
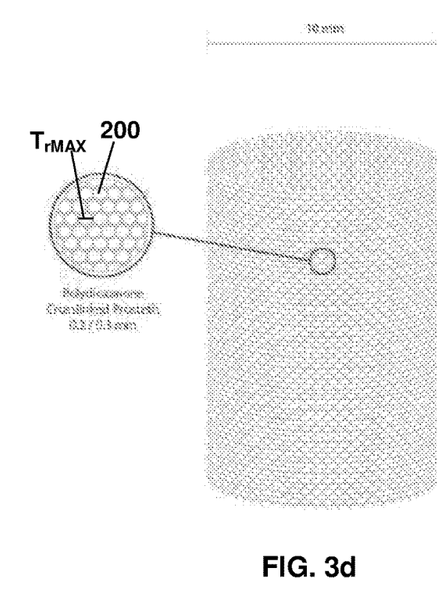

In the configuration of FIG. 3a, transverse wires 32 have each a curved configuration, in particular following a waved or sinusoidal pattern.

Preferably, transverse wires 32 connect with elements 311 of a strip 31 at the occurrence of maximal distance $d_{max}$ between adjacent elements 311.

In FIGS. 3a-3d, the prosthesis 1 is not subjected to stresses, i.e. it is shown in a non-implanted configuration or in an immediately post-operative configuration. In such configuration, transverse wires 32 are loose.

Figure 9A:
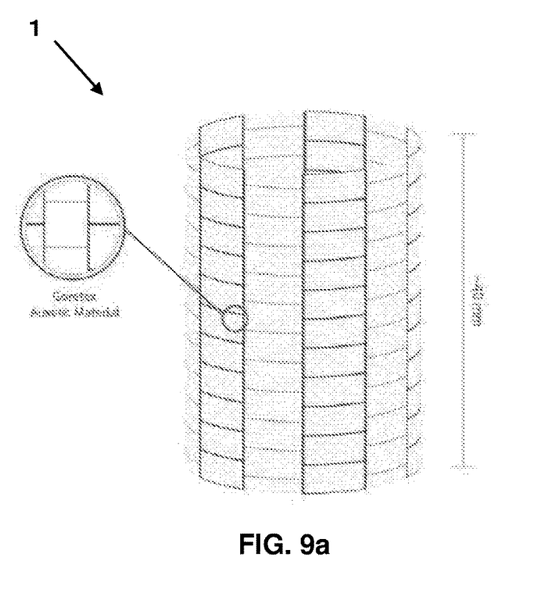
FIG. 9a shows a perspective view of the prosthesis of FIG. 3a in another configuration, corresponding to a longer period after its implantation.
Figure 9B:
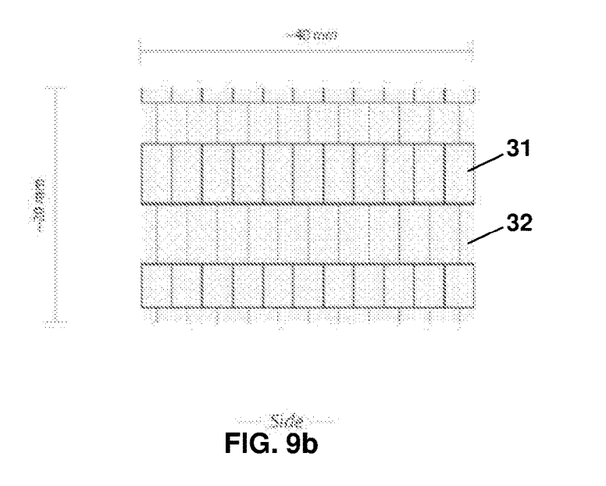
Figure 9C:
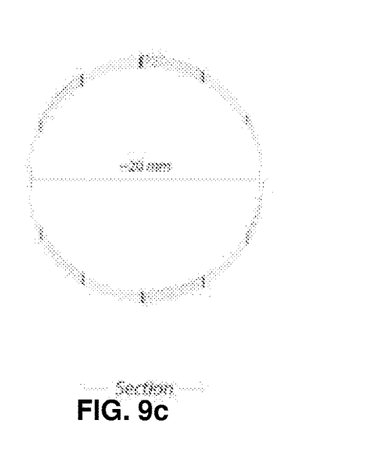
Figure 9D:
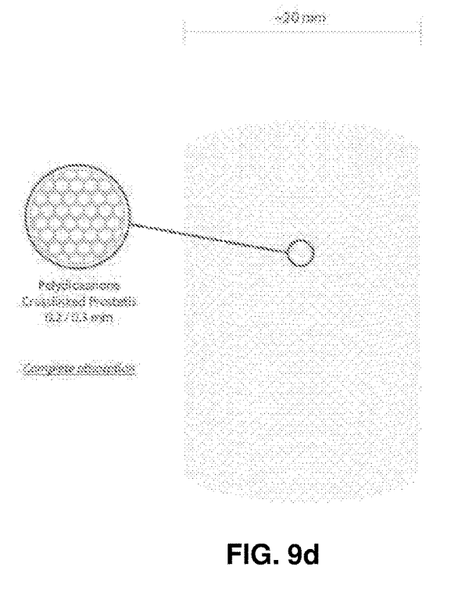

As visible by a comparison with FIG. 9a, preferably in a fully expanded configuration longitudinal elements 311 assume a straight pattern and are parallel to each other. Preferably, in such configuration transverse wires 32 are too fully straight and parallel to each other, in particular orthogonal to longitudinal elements 311 and/or strips 31.

The layer of auxetic material 3 is used to realize the longitudinal strips 31 as a deformable matrix (composite crosslinked prosthesis), so as to orient in the same way the polymer chains and thus make the overall structure compact.

Preferably, the layer of bio-absorbable material 2 is oriented to allow a maximum extensibility in the longitudinal direction (which allows growth in length) and a minimum transverse extensibility (limiting the enlargement of the diameter).

The same layer structure described above, in particular in conjunction with FIGS. 3a-3d, can apply also for an endovascular prosthesis, inverting the position of layers 2 and 3.

Experimentally, the layer of bio-absorbable material 2 of prosthesis 1 may be prepared at the operating table (in a time interval of 10+/−2 min) and designed to minimize radial tension. In one experiment, the cross-linked semiresorbable scaffold copolymer made by a single polydioxanone layer strengthened by an interlaced GORETEX 4-0 suture has been cut into a rectangle measuring 20 mm in height corresponding to the height of the pulmonary autograft, rolled on a metallic candle, and then fixed with a suture, so as to create a cylinder with an internal diameter of 10 mm (20 mm height and 10 mm diameter). The autograft was then inserted into the fibrillar cylinder and was anastomosed, suturing both its margins and those of the final prosthetic structure to the pulmonary autograft trunk.

This method of manufacturing can be applied also to an intravascular prosthesis.

The functioning of extravascular prosthesis 1 described above is as follows.

With particular reference to FIGS. 8a-8d and 9a-9d, it is observed that the form of prosthesis 1 tends to change over time with respect to the extravascular configuration assumed in post-operative phase (the latter shown in FIGS. 3a-3d).

More particularly, it is noted (by referring to FIGS. 8a-8d) that the layer of bio-absorbable material 2 is partially reabsorbed, reducing, but not eliminating, its containment function, while the layer of auxetic material 3 modifies its own form. In fact, the expanded polytetrafluoroethylene longitudinal strips 31 stretch by virtue of the auxetic properties of said material, while the transverse wires 32 begin to expand, as a result of the movement of the longitudinal strips 31, so that said prosthesis 1 will progressively adapt to the gradually enlarged form of the vessel, compensating the rigid containment function. The layer of auxetic material 3 can compensate for the stresses related to blood pressure, accompanying the growth process of the vase with its geometric changes, adjusting the gradual resorption of the scaffold, i.e. of the layer of bio-absorbable material 2.

Moreover, the latter, during the resorption, has also an active role in warrantying the elasticity of the vessel, thanks to the structural changes of the extracellular matrix induced by resorption of polydioxanone. The auxetic properties of this layer 3 preserve the dilation of the pulmonary autograft, subjected to systemic pressure, ensuring a physiological growth.

Said layer of auxetic material 3 performs, therefore, an active mechanical function, but it is biologically passive.

The scaffold, i.e. the layer of bio-absorbable material 2, which in this embodiment is polydioxanone, performs, under the mechanical profile, a marginal role and in each case connected or limited to the moment immediately subsequent to the implantation of prosthesis 1.

Conversely, from a biological standpoint, the layer of bio-absorbable material 2 stimulates, with its reabsorption, the extracellular matrix and the endogenous reserves present in it to get those biological changes that lead to a process of complete and homogeneous arterialisation of the vessel. In this process, the layer of bio-absorbable material 2 stimulates cells called fibroblasts, obtaining a more elastic and homogeneous vascular tissue, with the consequent pulmonary arterialisation of the autograph during the Ross procedure.

In FIGS. 9a-9d the prosthesis 1 is shown placed extravascularly after about six months. The bio-resorbable material layer 2 is substantially completely resorbed and the layer of auxetic material 3 shows a complete elongation of the longitudinal strips 31 and the full tension of the transverse wires 32.

It should be considered that the resorption of polydioxanone takes place in about three months and at six months there is no trace of this compound. In this way, the scaffold of the prosthesis 1, following the promoted changes, biodegrades completely.

Figure 10:
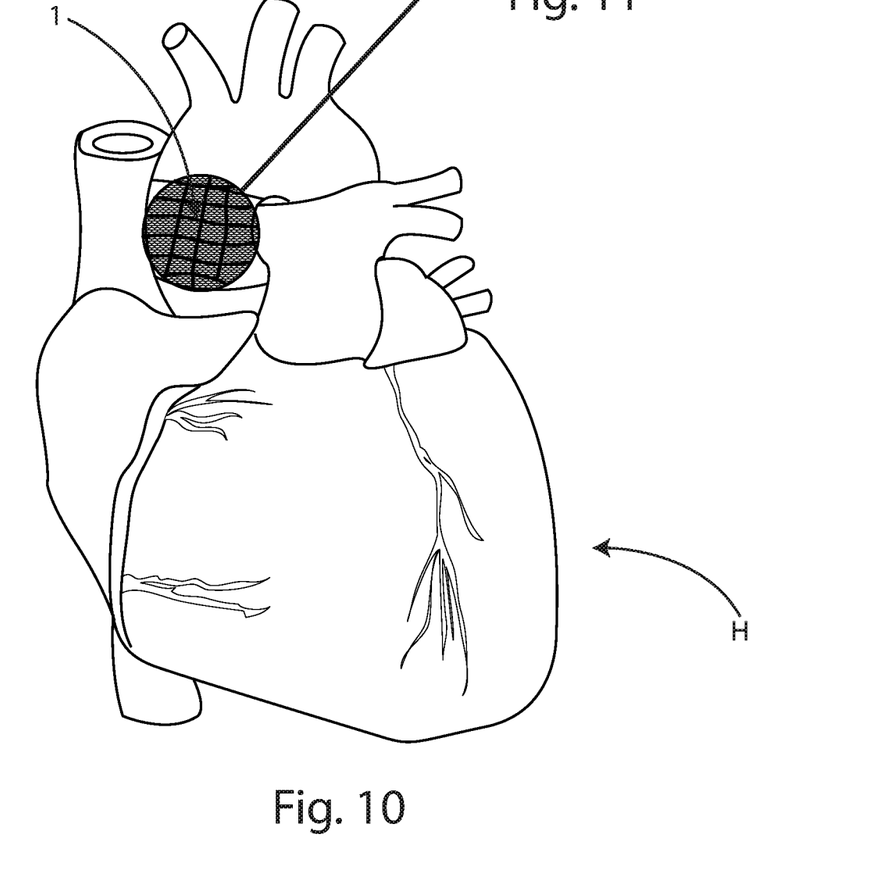
FIG. 10 shows a heart to which is applied an extravascular prosthesis according to a preferred embodiment of the present invention.
Figure 11:
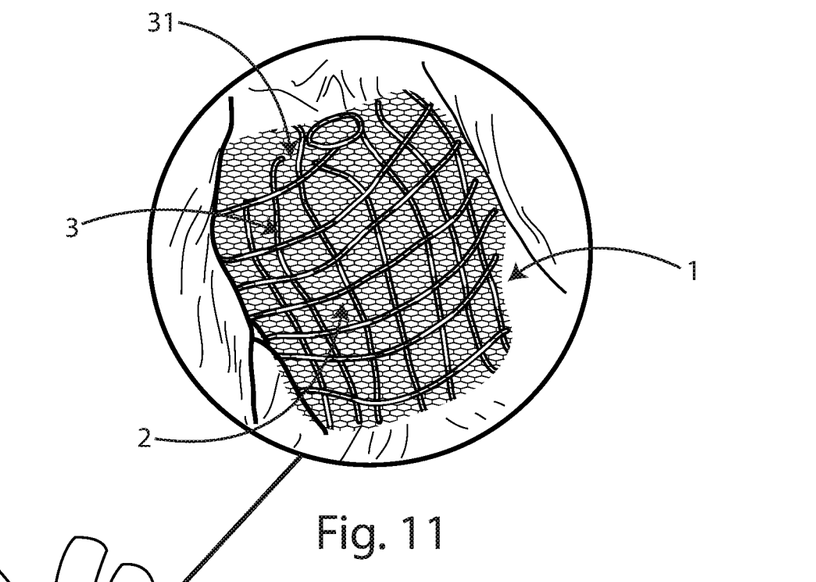
FIG. 11 shows a detail of FIG. 10.

Referring now to FIGS. 10 and 11, they show the application of prosthesis 1 extravascularly to a heart H subjected to a Ross procedure, in which it is observed, in particular, the arrangement of the prosthesis at the root of the aorta, where the reimplantation occurs.

Another advantage of the prosthesis 1 is to allow making a structure provided with windows to ensure the patency of the vascular branches during the implantation for the treatment of aneurysms or dissections of the thoracic and abdominal aorta.

Figure 12:
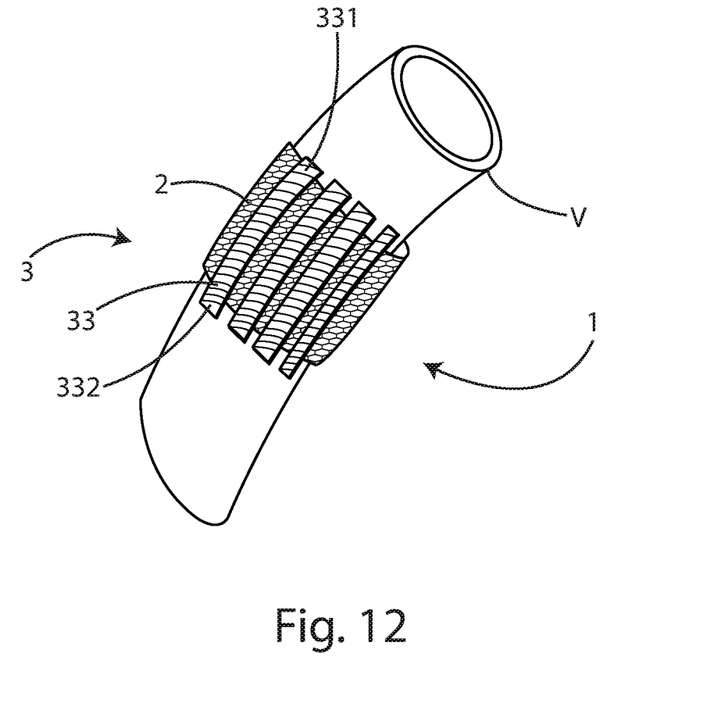
FIG. 12 shows schematically a further embodiment of a prosthesis according to the present invention.

FIG. 12 shows a further embodiment of extravascular prosthesis 1, wherein the layer of auxetic material 3 comprises a plurality of side longitudinal strips 33 not linked to each other, having ends 331 and 332.

When the prosthesis 1 of the present embodiment is applied to the blood vessel V, the bio-resorbable layer 2 is in contact with said vessel V, while each of said longitudinal strips 33 is disposed substantially longitudinally to the development of the vessel V, in such a way to be arranged above said layer of bio-absorbable material 2, and said ends 331 and 332 can be directly attached, for example by suturing, to said vessel V.

As far as endovascular prosthesis 1' is concerned, it presents the bio-absorbable material layer 2 disposed outside, in order to be coupled with the internal wall of the vessel, while the layer of auxetic material 3 is in the inner side of the lumen.

As said above, in a preferred embodiment the layer of bio-absorbable material 2, which acts as a scaffold, is made of polydioxanone or similar, such as poly-l-lactic acid, if necessary suitably treated with growth inhibitors and antiplatelet, whereas the layer of auxetic material 3 is made of expanded tetrafluoroethylene, preferably treated with polyethylene oxide (ENP).

Intravascular prosthesis 1' may have, as mentioned, a lattice structure for layer 2, with cells of hexagonal or other shape, less pronounced (i.e. with cells of larger dimensions, therefore with larger cell density) for small vessels, e.g. coronary and cerebral vessels, and more marked (i.e. with cells of lower dimensions, therefore with lower cell density) in large caliber vessels such as the aorta, wherein the solicitation of stress and strain (stress-strain) also at the internal inside is greater. This configuration allows overcoming the limitations of current stent, which, presenting a spiral configuration, tend to have a high percentage of long-term restenosis. This complication mandates for an alternative structure which results in less turbulence, as the one proposed.

In a further embodiment, the intravascular stent (endovascular prosthesis 1') for the arteries of size between about 2 mm-0.8 cm have also a further layer of a central reinforcement (not shown in the figures) made of titanium or nickel coated by a sheet of auxetic material 3, for example made of expanded tetrafluoroethylene treated with polyethylene oxide (ENP).

In other words, the endovascular prosthesis 1' would be composed from outside to inside as follows:
- external scaffold made of bio-resorbable polydioxanone layer 2 or other similar materials;
- a reinforcement layer of platinum, titanium or nickel or gold; and
- the layer of auxetic material 3, made of expanded tetrafluoroethylene treated polyethylene oxide (ENP).

For small vessels (e.g. arteries having a diameter comprised from 2 mm to 0.8 cm) the layer of bio-absorbable material 2 is preferably functionalized, in order to release substances with inhibitory action on cell proliferation and on platelet aggregation.

Therefore, a further advantage of the present invention is to allow the realization of absorbable stents to limit the side effects of a long-term treatment with antiplatelet drugs.

As mentioned above, the endovascular version of the prosthesis is intended to be used as stent in vessel subjected to aneurysmal degeneration as aorta or small cerebral arteries. Above-mentioned stent includes a central core of platinum, nickel or titanium and the cross-linked layers of PDS and ePTFE with the polydioxanone in direct contact with the endothelium and ePTFE frame in external position. The layer of bio-absorbable material of prosthesis may be prepared and designed to minimize radial tension and to promote while the GORETEX stent is right to changes of load pressure. The size of the endoprosthesis are variable depending on the size of the vascular structure to be treated.

Implantation of prosthesis 1' can take place by means of a standard procedure based upon expansion of a balloon carrying the prosthesis into the vascular structure.

As mentioned above, auxetic materials, as expanded Polytetrafluoethylene (ePTFE), are characterized by a negative Poisson's ratio that is—when stretched—they become thicker perpendicular to the applied load. This counterintuitive behaviour can be observed at different scale levels—from single molecules to macroscopic matter—and generally can be traced into a particular internal material microstructure, often made of interconnected thin elements arranged to form re-entrant hexagonal patterns, which confer to the overall material response mechanical properties such as high deformability, high-energy absorption and somewhat high fracture resistance.

In the embodiments presented, the auxetic material (and behavior) has been obtained by means of a structural weave characterized by a negative Poisson's ratio, made of e-PTFE, also known as GORE-TEX. This structure was combined with a PDS one in order to create a prosthetic system able to accommodate mechanical loads due to systemic pressure, guaranteeing autograft integrity and controlling the progressive graft dilation. The rationale of this approach relies in the possibility to maintain and enhance the positive biological effects on vessel wall remodelling, previously shown with resorbable materials, providing additional stabilization of the neoartic root through the use of a tailored ePTFE mesh, which allows regional somatic growth and prevents dilatative degeneration.

To better define, even in quantity, the above properties of prosthesis 1 or 1', a formal mathematical model has been developed (see below) with aims to illustrate its performance. This model was created on the basis of experimental findings and preliminary research on replacement of the thoracic aorta with a pulmonary autograft in growing animals. The prosthesis was implemented according to the embodiment shown in FIG. 1.

In particular, the model is based on the Hook's law, considering that the resorbable material can profoundly affect the elasto-mechanical properties of the neoaortic root, conferring resistance to dilatation and a behavior of conformability.

$$\Delta \ell = \frac{1}{E} \ell \frac{F}{S}$$

Where in E is the Young's modulus and l is the length of the contour.

$$\Delta \ell = \frac{1}{E} \ell \frac{F}{S} \Rightarrow \vartheta = E\varepsilon$$

Consequently, the stress is:

$$\vartheta = \frac{F}{S} \ell$$

Instead, the deformation is:

$$E = \frac{\Delta \ell}{\ell}$$

The pulmonary autograft in the context of the surgical Ross procedure (Ross free standing Root Replacement) according to Hook's law can be considered as an actual distensible cylinder and is subjected to stress and strain forces and to an elastic tension. As an extensible solid cylinder the Hooke's law for linear-elastic bodies and membranes might be applied.

The mathematical model, based on three concepts, foresees:
the stress-strain curves;
the elastic tension;
the balance of Laplace (Laplace equilibrium).

Figure 4:
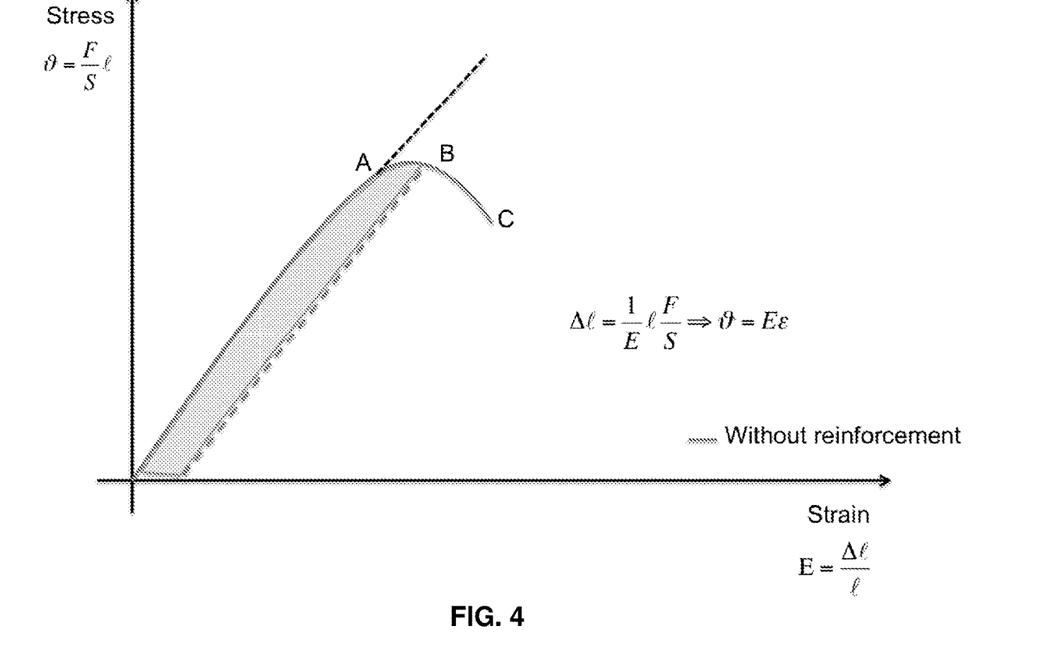
FIG. 4 shows a graph that depicts the relationship between the stress and the deformation of a known art prosthesis without any bio-resorbable material reinforcing layer.
Figure 5:
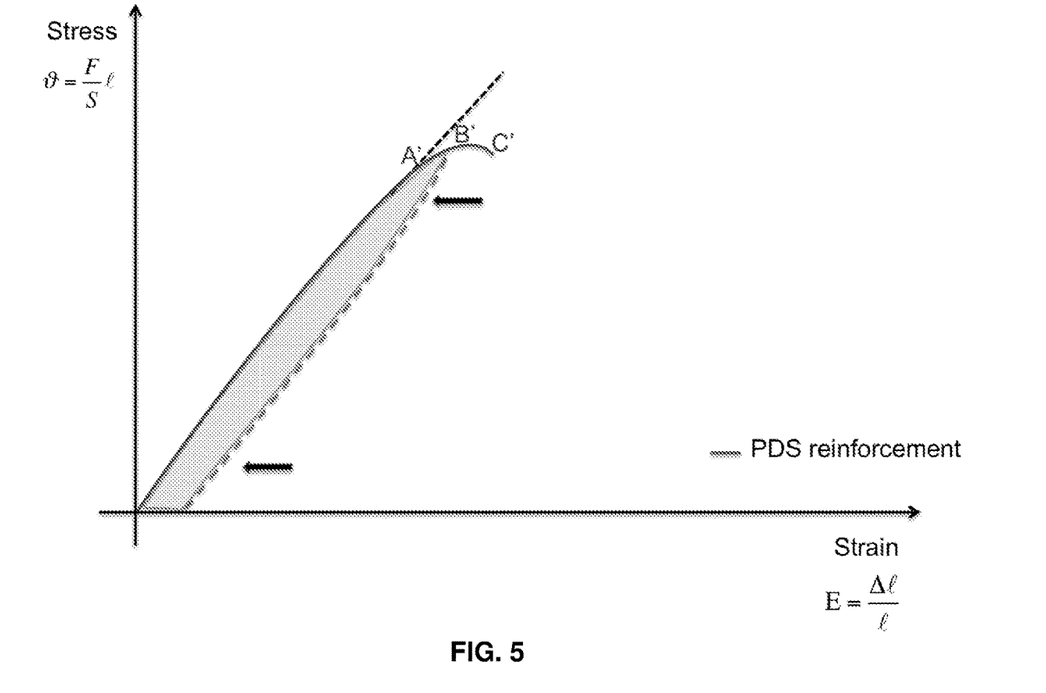
FIG. 5 shows a graph that depicts the relationship between the stress and the deformation of a prosthesis according to a preferred embodiment of the invention, having a bio-resorbable material reinforcing layer.

According to our angiographic measurements and on the basis of the histological results the Inventor was able to extrapolate a stress strain curve (FIG. 4) representing the relationship between the stress a and the deformation to which the PA is subjected. FIG. 4 depicts the behaviour of the non-reinforced PA, with A indicating the traits of elastic behaviour, B the non-elastic behaviour and C the point of rupture. The region included under ABC represents the non-elastic region. The release phase (hysteresis) starts before the point B. Conversely, when a crosslinked bio-resorbable prosthesis realized in PDS is applied on the system the curve modifies towards a more elastic behaviour, as represented in FIG. 5, with A', B' and C' showing respectively the elastic behaviour, the non-elastic and the breakage of the bio-resorbable prosthesis. Therefore, application of a bio-resorbable reinforcement is able to modify the behaviour of the curve of distensible materials, such as vessels wall, obtaining an increase of their elastic properties. This is observed in the curve as the shift of A towards A' (increased elasticity and compliance) and of the maximum distensibility point C towards C', as the reinforcement effectively prevented massive dilation. This provokes a reduction in the critical area determined by the fall of the curve (FIG. 5).

The mechanisms underlying this phenomenon might be found in the application of the Hooke's Law to distensible membranes, as the PA conduit, in terms of elastic tension. The elastic tension for a solid is dependent on the surface and on its intrinsic characteristic (i.e. vessel wall properties). When the PA is transposed in aortic position, the systemic pressure determines a conversion of the elastic tension in elastic potential energy (U) according to following formula:

$$\Theta = \Theta(S) = \frac{\Delta \Box(S)}{\Delta S} = \frac{\Delta l}{\Delta S} \rightarrow U = U(S) = \Theta(S)\Delta S.$$

Figure 6:
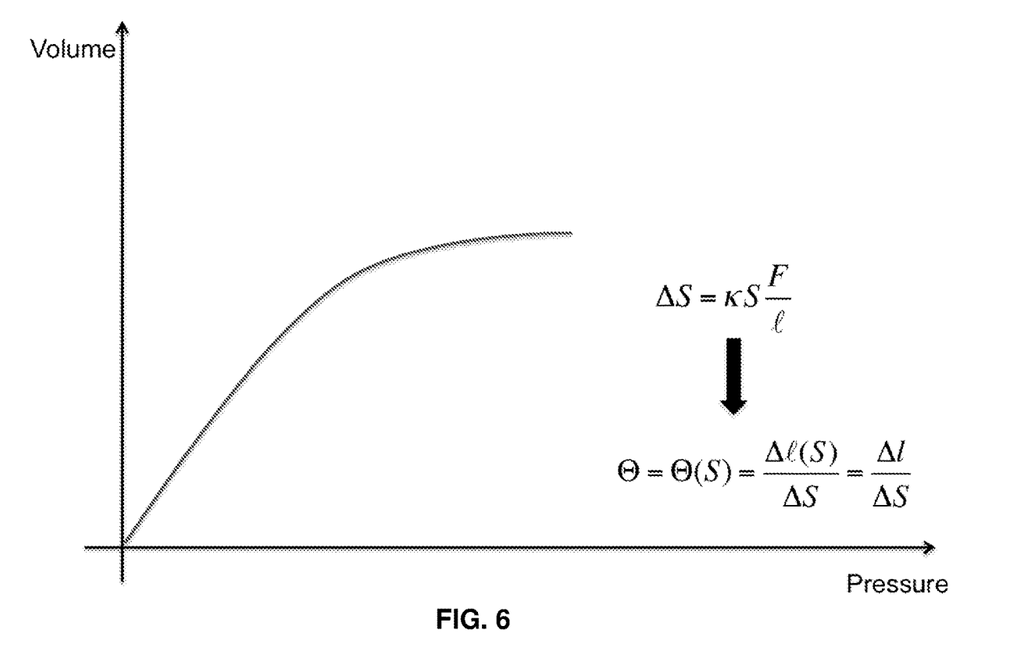
FIG. 6 shows a graph that depicts the relationship between the volume and the pressure applied onto a known art prosthesis without any bio-resorbable material reinforcing layer.
Figure 7:
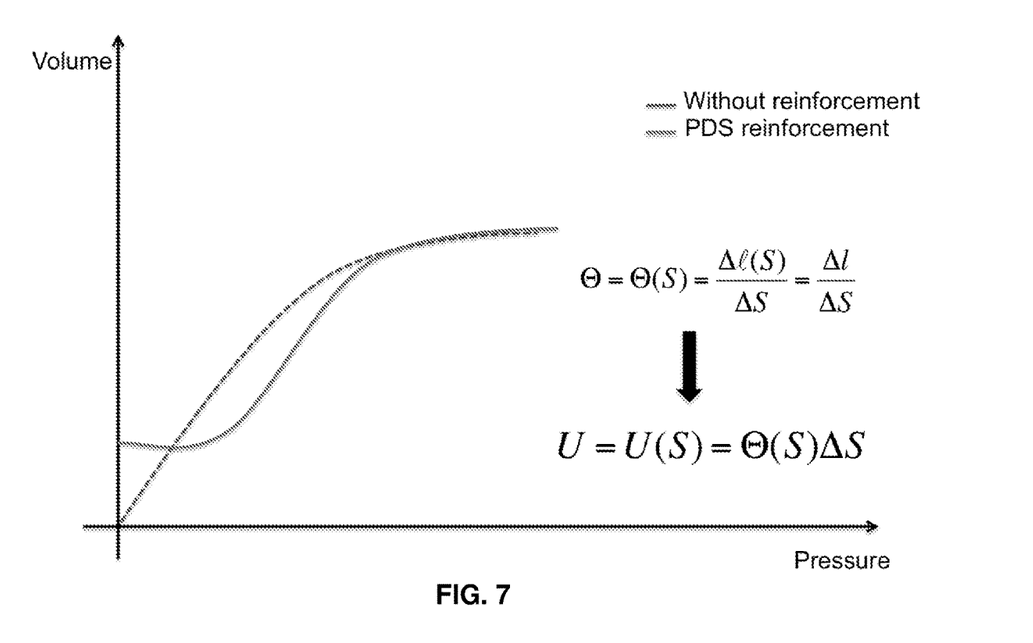
FIG. 7 shows a graph that depicts the relationship between the volume and the pressure applied onto a prosthesis according to a preferred embodiment of the invention, having a bio-resorbable material reinforcing layer.
Figure 8A:
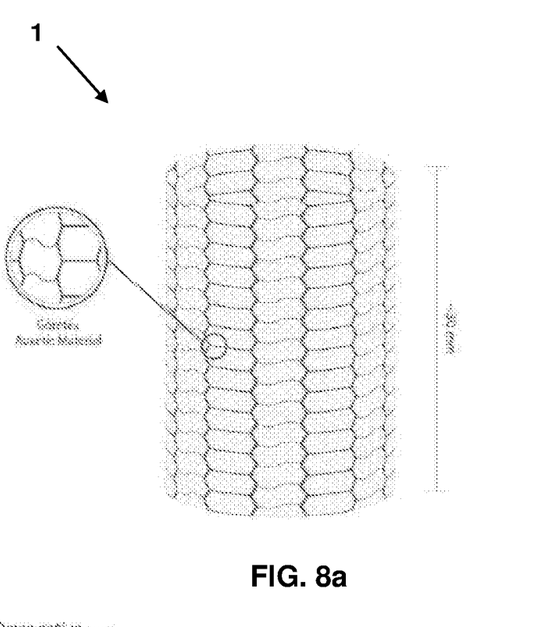
FIG. 8a shows a perspective view of the prosthesis of FIG. 3a in an intermediate configuration, in particular a few months after its implantation.
Figure 8B:
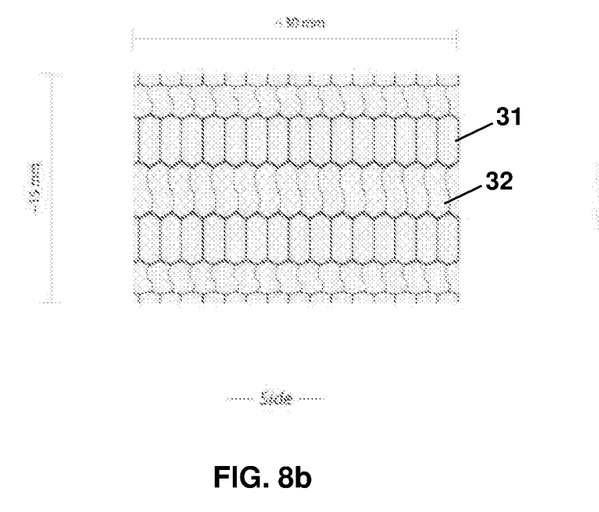
Figure 8C:
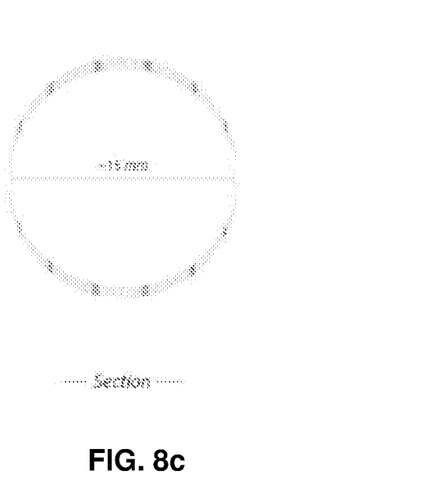
Figure 8D:
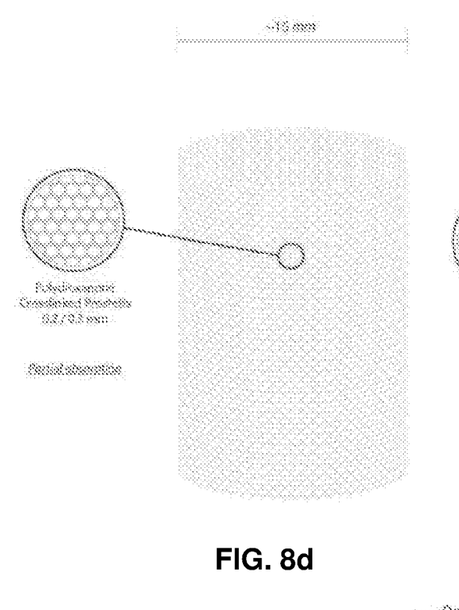

Therefore, the potential elastic energy (U) depends on the extension of the surface (S) and on the composition of the material constituting the cylinder including the intramolecular cohesion forces. The Inventor demonstrated histologically that during the resorption process of a PDS scaffold applied to PA, a remodeling process of the vessel wall occurs, resulting in a more dense connectival architecture of the tunica media with an increase in its elastic component. The Inventor submits that this phenomenon fits in the mathematical model and that the bio-resorbable prosthesis increased both the surface area of the neoaortic membrane and, at the same time, being resorbed within the PA, modified both the forces of cohesion and the elastic characteristics of the membrane (FIGS. 6 and 7). Molecular structure of PDS is characterized by repetition of fundamental units with a cristallinity of 55% circa, being likely to increase the intramolecular cohesion forces.

The autograft morphological and geometrical features, its non-homogeneous elastic characteristics and the time-evolution of the mechanical properties and deformation processes expected during growth and remodeling of the tissue, in both reinforced and not reinforced cases, contribute to draw a complex dynamics.

Nevertheless, some ad hoc simplified schemes, governed by suitable geometrical and mechanical parameters, can be realized to catch some key factors which mainly influence the biomechanical response of both reinforced and not-reinforced pulmonary autografts under the action of the systemic pressure. In particular, by making reference to overall mechanical properties and mean initial autograft diameter d and wall thickness t of an equivalent elastic cylindrical tube (see for example the comprehensive work on growth and elasticity of arterial walls by Holzapfel and Ogden G. A. Holzapfel and R. W. Ogden, "Constitutive modelling of arteries," Proceedings of the Royal Society of London A: Mathematical, Physical and Engineering Sciences, vol. 466, pp. 1551-1597, 2010) under the hypothesis of neo-Hookean incompressible hyperelastic behavior and exploiting the Laplace formula, one can mathematically derive the following relationship between the internal pressure p and the final deformed diameter D through the circumferential stress s:

$$p = s \times \frac{2T}{D} \Rightarrow p = G \times \left[1 - \left(\frac{d}{D}\right)^4\right] \times \frac{2t}{d}$$

where T is the final thickness and G is the Lame elastic shear modulus.

The aortic root anatomy presents an increased degree of complexity and cannot be approximated to a cylindric geometry. Additionally, as described above, material deformation occurs not only in axial and lateral fashions, but a shear stress modulus is also applied determining a sliding of the conduit components.

Clinical reports on the differential enlargement of the different sectors of the root and their potential for dilation (Horer J, Hanke T, Stierle U, Takkenberg J J, Bogers A J, Hemmer W, et al. *Neoaortic root diameters and aortic regurgitation in children after the Ross operation. Ann Thorac Surg.* 2009; 88:594-600) brought the Inventor to reconsider the PA reinforcement strategy on the basis of the mathematical model developed and on our initial experience on resorbable reinforcement. The major disadvantages of synthetic materials used in pediatric cardiovascular surgery regard the inability to adapt to the vessels during their structural development and growth, and the induction of a strong inflammatory reaction which affects the viability of the autografts interfering with the normal process of arterialization, and impairs their elastic compliance (Carel J *Thorac Cardiovasc Surg.* 2008; 136:472-5). For these reasons the selected material is suitable to comply with both shear modulus requirements and differential dilation tendency of the root. ePFTE is a material currently used in surgery and known, from the elastomechanical standpoint, to have a so-called auxetic behaviour. Its Poisson's ratio, i.e. the parameter to describe ability of a material to respond to applied forces, is negative which provides it with extremely advantageous compliance properties. ePTFE fibers, if subjected to a tensile stress, "open up" structurally and expand in the direction transverse to the stress; conversely, if these materials are subjected to compression they "close" structurally. As shown in the Figures introduced above, the Inventor designed a specific ePTFE external armour not in direct contact with the vessel wall, which would progressively allow multidirectional growth and resistance to dilatation over time.

The plurality of interconnected transverse and longitudinal wires constitutes a mechanism to adapt to longitudinal growth and dilation going progressively from a "loose" to an "extended" configuration. The specific weave design would be therefore able to address issues of differential tendency to dilation of the different component of the aortic root. In this context, the resorbable material used, PDS, plays a key role in the architecture of the proposed prosthesis system. It works on two levels: at the early stage, its mechanical properties serve to add elastic stiffness to the trunk for confining exceeding vessel dilation phenomena and avoiding aneurisms; successively, during its degradation process, the PDS slowly abandons its initial stiffening role to allow pressure-induced PA tissue remodeling and growth which will finally lead to the vessel arterialization, the overall result depending on the synergy between the PDS and the e-PTFE materials. From the biomechanical standpoint, a virtuous cooperation between biological and synthetic materials takes place, a sort of "stress-shielding" phenomenon guiding the physiological arterialization of the vessel wall, which finally determines the success of the autograft system. In particular, the doubly reinforced pulmonary autograft prosthesis system would work as a sort of "relay race", by guaranteeing the handover of the bearing structure functions from the PDS scaffold (at the early stages of tissue growth and remodelling) to the e-PTFE armor, initially "dormant" as a consequence of the typically low stiffness exhibited by auxetic structures at small strain. In this way, the mechanical shielding of the lapse vessel contains the radial expansion and simultaneously allows to the pulmonary artery to remodel its tunics for attaining an adequate level of mechanical properties. Once the bioresorbable scaffold has completed its degradation program and the strengthened vessel walls can actively respond to the systolic pressure, the e-PTFE structure accompanies the PA media and adventitia toward their progressive aortic somatic growth, by stretching its weave to gain stiffness and effectively confine further vessel expansion, so avoiding tissue prolapse and aneurismal degenerative phenomena.

Interestingly, at the end of the study (6 months) the Inventor obtained in the reinforced group neoaortic diameters comparable with those reported by Bonhoeffer et al in the ascending aorta of juvenile lambs at the same age (*Circulation.* 2000; 102:813-6.). This point might acquire an additional relevance considering that in the Ross procedure the pulmonary trunk is not transposed into the descending aorta (as in this experimental model) but in the aortic root and the ascending aorta diameter represents the most accurate reference point to be taken as it is the site of the actual anastomosis with the PA and more accurately reflects the clinical situation.

Additionally, a non-linear Gompertzian-like growth profile of the reinforced graft diameter and walls have been actually experimentally found, showing that the velocity of the process at hand varies with time and—in the case of reinforced pulmonary autograft—the sizes asymptotically tend to stabilize around physiological dimensions of the control.

In the graph of FIG. 7*bis* the growth versus time, in the observation interval of 1 day—six months, is depicted.

The graphic shows the evolution of the outer diameters (continuous lines represent theoretical outcomes while markers are experimental measures). Notably, a sort of asymptotic behavior is observed that seems to stabilize the vessel diameter of the reinforced autograft as the time approaches month 6.

The model developed above is, of course, meant to explain the behavior of prostheses 1 or 1', as described qualitatively in FIGS. 4, 5, 6 and 7.

With particular attention to the process of resorption of polydioxanone, it is observed as it occurs from three to six months, after which there is no trace of this compound. The role of scaffold is precisely to elicit a phenomenon of histoarchitectuaral rearrangement of the pulmonary autograft resulting in medial thickening of the vessel and in an increase in elastic wall component leading to the formation of a neovassel with characteristics similar to the native aorta. The polydioxanone has approximately 55% crystallinity and a glass transition temperature ranging between −10° C. and 0° C. Moreover, it is a material that has a regular repetition of a basic unit, which merge into folded chains in dense regions called crystallites. These are joined together by so-called "crosslinks" giving the polymer a higher tensile strength and a very high elastic modulus when compared to that in the corresponding amorphous form. All this is in relation to the degree of compactness of the polymer. Since no polymer can be organized in a totally crystalline structure, even though it may have a high crystallinity, there will always be some partially amorphous regions inside.

The polydioxanone, among other things, is a polymer with a high average molecular weight, very viscous, with a slower biodegradation in respect to those with lower molecular weight and lower viscosity.

For the use in question, the temperature has a very important role as regards the properties of the material. In fact, the biodegradation of polydioxanone is firstly occurring with the loss of molecular weight and loss of strength of the material.

The initial phase of the degradation is chemical in nature. The biological process and the total removal of the material, however, occur later.

The polymer of polydioxanone degrades mainly in two ways: by chain scission and by dissolution.

The polydioxanone, having hydrophilic domains, dissolves during normal physiological processes when solvent molecules, such as water, are absorbed in the polymer and are small enough to occupy the space between the chains of the macromolecules. In this case they act as plasticizers, making the material more ductile as they reduce the number of secondary bonds between the chains.

Moreover, the crystallinity of the polymer can be altered. Both the mechanical and thermal properties (for example the glass transition temperature) can be influenced by the absorption of solvent molecules. In extreme cases, the chains are quite soluble and remain few covalent bonds between the chains and the polymer can then dissolve completely.

The chain scission involves the breakage of primary bonds, rather than secondary ones. There is, therefore, a separation between the chain segments on the point of breakage of the bond, which entails a reduction of the molecular weight, which can have, as in the case of dissolution, significant consequences on the mechanical properties and thermal properties.

The chain scission may occur due to hydrolysis or by oxidation. Regarding the hydrolysis, water molecules enter the implanted material, causing cleavage of molecular bonds between the monomers. This leads to the scission of the polymer chains into shorter chains. The main factors that produce the extension of the hydrolysis in polymers are:

The reactivity of the functional groups of the main part of the polymer;
The extent of interchain bonds;
The increase of the water available for the polymer.

Oxidation is a process in which reactive species (usually free radicals) attack and break the covalent bonds that hold the chains. The main factors that affect the oxidation are mostly the first two mentioned above for the hydrolysis.

The degradation of this copolymer is made by splitting their ester chains.

The polydioxanone is cleaved into glyoxylate, excreted in the urine, or converted to glycine and subsequently, as polyglycolic acid (PGA), transformed into water and carbon dioxide. In any case, both polyglycolic acid and polydioxanone follow the same final cycle (from pyruvate onwards) of the polylactic acid (or PLA). The degradation time, as already mentioned, depends on the porosity of the copolymer, the crystallinity, and molecular weight.

Experimental Section

Prosthetic Device

The device consisted of an internal resorbable scaffold made with Polydioxanone (PDS) and an external non-resorbable layer of expanded polytetrafluoroethylene (ePTFE). PDS layer was arranged in a frame of hexagonal cells reinforced by an external armour of ePTFE. The layer of ePTFE was coupled externally to the bio-absorbable material and comprises a plurality of side longitudinal strips, having an auxetic behaviour, and a plurality of transverse wires, which connect each longitudinal strip with the two adjacent. The layer of auxetic material was realized as a deformable matrix and applied to the bioresorbable material The layer of bio-absorbable material was constructed to embrace the root of the aorta allowing its multidirectional growth.

Animal Model

Transposition of pulmonary trunk in aortic position was performed in 20 growing lambs as previously described in the state of the art. For this study, animals 8-10 weeks old with an average weight of 21±3 Kg were used. Morphometric and cardiovascular parameters were comparable preoperatively among animals. There were no difference in hemoglobin levels and ventricular function. Briefly, anesthesia was induced with sodium thiopentothal (6-8 mg/kg) via the internal jugular maintained with isoflurane (1% to 2, 5%) inhalation. Animals were intubated and received 100 mg of lidocaine as prophylaxis against rhythm disturbance. Heart was approached through left thoracotomy and cardiopulmonary bypass established between descending aorta and right atrium. The cerebral circulation of the animal was maintained on a beating heart. Pulmonary trunk was harvested and transposed into the descending aorta with an end-to-end anastomosis in 5-0 Prolene. A fresh pulmonary artery homograft, explanted from animals sacrificed on the same day for another experimental study, was inserted to reconstruct the right outflow tract, with a proximal and distal end-to-end anastomosis in 5-0 Prolene, as in the Ross operation. 10 lambs received a reinforcement of the pulmonary autograft (PA) by the prosthetic device. The PA was inserted into the device and was anastomosed, suturing both its margins and those of prosthetic structure to the PA trunk. 10 additional animals did not receive any reinforcement and served as control non-reinforced group. All animal experiments have been performed in respect of guidelines for animal care and handling and the protocol was approved by the institutional animal care committee.

Data Acquisition

Animals were assessed with angiography and echocardiography at two time points, at day 0 (D0) and 6 months (M6) postoperatively, respectively. Selection of this time frame has been guided by two main points. Firstly, 6 months is the time approximately required for lambs to reach a weight of 60 Kg, which might reliably reflect the body mass of the average human patients normally undergoing Ross operations. Secondly, considering the aim to investigate the effect of a resorbable reinforcement and the time for resorption reported for PDS, the endpoint of 6 months was selected as it might reliably have allowed time enough to complete the resorption process. This would have permitted to analyse histologically the samples after a total resorption of the PDS applied. Three averaged echocardiographic and angiographic measurements were taken by two independent observers blinded in regard to the treatment group. An interrater reliability analysis using the Kappa statistic was performed to determine consistency among raters. K coefficient was 0.82 indicating adequate agreement. Eventually, animals were humanely sacrificed and tissue harvested for histopathological analysis. Measurements of the ascending aorta, descending aorta proximally and distally to the autograft were made in order to obtain a reference to be compared to the diameter of the PA. Hematoxylin Eosin, Masson's Thrichrome, Mallory and Picrosirius red stainings were performed after explantation. Further immunohistochemistry for MMP-9 was also performed to elucidate extracellular matrix remodelling phenomena. Continuous variables were compared using paired Student's t-test. P values less than 0.05 (two-tailed) were taken to indicate statistical significance. Analysis was performed with the SPSS version 20.0 software for Mac.

Results

According to growth curve animal weights was doubled (21±3 kg at D0 and 45±7 kg at 6 months). In the Control group two animals died because of aneurysmatic rupture of the PA, while in the reinforced group there was no mortality. In the control group, PA distension (28±2 mm) was immediately noted, followed by aneurysm development at M6 (40±2 mm, P<0.0001 vs. reference, 57% diameter increase with respect to D0). In the reinforced group an initial dilation to 18±1 mm was detected and final diameter of 27±2 mm (42% increase). Similarly, echocardiography showed immediate burst dilation of the control with diameter of 31±2 mm and late aneurysmal degeneration 42±3 mm. The reinforced group maintained 17±3 mm immediately after implantation and 29±4 mm at M6.

At macroscopic analysis, specimens from control group were severely dilated with intimal thinning and intraluminal thrombus. Two ruptures have been detected. Conversely, reinforced PA did not show particular abnormalities macroscopically. At histology, medial disruption with connective fibrous replacement of muscular layers and lymphoid infiltrates could be noticed in the non-reinforced group. In the reinforced group compensatory intimal hyperplasia was present in absence of intimal tears and remnants of the slowly resorbable PDS suture could be detected in the adventitia. Importantly, Trichrome Masson's showed a rearrangement of the tunica media which displayed a dense fibrous network mainly constituted by elastin organized in concentric lamellae suggesting an elastic remodelling phenomenon of the PA. Specific staining confirmed increased content of elastin in respect to control, with fibers organized in a compact layer at the level of the "elastic zone" of the vessel. In parallel, reinforced PA showed an overexpression of MMP-9 in respect to control suggesting an underlying process of extracellular matrix remodeling and confirming the impression of an elastic remodeling and arterialization. Additionally, inflammatory infiltrate was scarce with rare macrophages or monocytes colonizing the reinforced arterial wall, reliably suggesting that the biomaterial did not elicit an exuberant inflammatory foreign-body reaction over time.

The present invention has been described for illustrative but not limitative purposes, according to its preferred embodiments, but it is to be understood that those skilled in the art may make variations and/or modifications without departing from the relative scope of protection, as defined by the appended claims.

The invention claimed is:

1. A prosthesis (1, 1') for organs with lumens, which prosthesis comprises:
   at least one bio-absorbable material layer (2), configured to be arranged in contact with said lumen organ when said prosthesis (1, 1') is implanted,
   at least one auxetic material layer (3), arranged in contact with and within said at least one bio-absorbable material layer (2), and
   a reinforcing layer, said reinforcing layer being coated by said auxetic material layer (3),
   wherein said prosthesis (1') being usable as an endovascular prosthesis, which prosthesis is a stent:
   wherein said bio-absorbable material layer (2) is a mesh having a plurality of polygonally-shaped cells,
   wherein said bio-absorbable material layer (2) comprises polydioxanone (PDS),
   wherein said auxetic material layer (3) comprises a plurality of side longitudinal strips (31), arranged in parallel having an auxetic behavior in the longitudinal development direction,
   wherein said auxetic material layer (3) comprises expanded polytetrafluoroethylene (Goretex®), and
   wherein said reinforcing layer is made of metal.

2. The prosthesis (1, 1') according to claim 1, wherein said bio-absorbable material layer (2) further comprises polyglycolic acid and/or acid and/or poly-l-lactic acid and/or the poliglactin (Vicril®) and/or the copolymer poly-1-lactic acid co-ε-caprolactone.

3. The prosthesis (1, 1') according to claim 1, wherein said bio-absorbable material layer (2) is capable to release gradual release drugs and/or substances having inhibitory action on cell proliferation and/or platelet aggregation.

4. The prosthesis (1, 1') according to claim 1, wherein each cell of said bio-absorbable material layer (2) has a maximal transverse dimension comprised in a range 0.2-0.3 mm.

5. The prosthesis (1, 1') according to claim 1, wherein said auxetic material layer (3) comprises expanded polytetrafluoroethylene (expanded PTFE, Goretex®) treated with polyethylene oxide (ENP).

6. The prosthesis (1, 1') according to claim 1, wherein said bio-absorbable material layer (2) and/or said auxetic material layer (3) has a substantially cylindrical shape.

7. The prosthesis (1) according to claim 1, wherein said bio-absorbable material layer (2) is arranged within said auxetic material layer (3), said prosthesis (1) being usable as extravascular prosthesis.

8. The prosthesis (1, 1') according to claim 1, wherein said auxetic material layer (3) comprises a plurality of transverse wires (32), which connect each of said longitudinal strips (31) with the adjacent longitudinal strips (31), such that, when said prosthesis (1, 1') is not subject to stresses, said transverse wires are loose, following a curved pattern.

9. The prosthesis (1) according to claim 1, wherein each longitudinal strip (31) has a bellows-like structure which makes the strip extensible in the longitudinal direction.

10. The prosthesis (1) according to claim 1, wherein the ends of said side longitudinal strips (31) are configured to be fixed to the lateral wall of the organ with lumen in which said prosthesis (1) is applicable.

11. A surgical method comprising a step of implanting a portion of an autologous pulmonary artery to replace an aortic root, which method provides a further step of implanting an extravascular prosthesis according to claim 1 as a support for said portion of pulmonary artery, wherein said method preferably follows a Ross procedure.

12. A surgical method comprising a step of implanting an endoprosthesis according to claim 1.

13. The prosthesis (1, 1') according to claim 1, wherein said plurality of polygonally-shaped cells comprises hexagonal cells.

* * * * *